United States Patent
Nicholas et al.

(10) Patent No.: US 8,247,631 B2
(45) Date of Patent: Aug. 21, 2012

(54) PROCESS FOR CATALYTIC CRACKING OF HYDROCARBONS USING UZM-35

(75) Inventors: Christopher P Nicholas, Evanston, IL (US); Deng-Yang Jan, Elk Grove Village, IL (US); Jaime G. Moscoso, Mount Prospect, IL (US)

(73) Assignee: UOP LLC, Des Plaines, IL (US)

( * ) Notice: Subject to any disclaimer, the term of this patent is extended or adjusted under 35 U.S.C. 154(b) by 249 days.

(21) Appl. No.: 12/820,095

(22) Filed: Jun. 21, 2010

(65) Prior Publication Data

US 2011/0308998 A1 Dec. 22, 2011

(51) Int. Cl.
*C07C 4/06* (2006.01)
*C10G 11/00* (2006.01)

(52) U.S. Cl. .............. 585/653; 208/120.01; 208/120.35

(58) Field of Classification Search .................. None
See application file for complete search history.

(56) References Cited

U.S. PATENT DOCUMENTS

| | | | |
|---|---|---|---|
| 4,310,440 A | 1/1982 | Wilson et al. | |
| 4,440,871 A | 4/1984 | Lok et al. | |
| 4,870,222 A | 9/1989 | Bakas et al. | |
| 4,910,006 A | 3/1990 | Zones et al. | |
| 4,963,337 A | 10/1990 | Zones | |
| 5,512,267 A | 4/1996 | Davis et al. | |
| 6,049,018 A | 4/2000 | Calabro et al. | |
| 6,183,699 B1 | 2/2001 | Lomas | |
| 6,310,265 B1 | 10/2001 | Chester et al. | |
| 6,506,953 B1 | 1/2003 | Cheng et al. | |
| 6,776,975 B2 | 8/2004 | Wilson et al. | |
| 7,198,711 B1 | 4/2007 | Chester et al. | |
| 7,578,993 B2 | 8/2009 | Lewis et al. | |
| 7,922,997 B2 | 4/2011 | Moscoso et al. | |
| 7,981,273 B2 * | 7/2011 | Nicholas et al. | 208/120.01 |
| 8,157,985 B2 * | 4/2012 | Nicholas et al. | 208/120.01 |
| 2005/0095195 A1 | 5/2005 | Lewis et al. | |
| 2007/0154387 A1 | 7/2007 | Johnson et al. | |
| 2010/0331594 A1 | 12/2010 | Nicholas et al. | |

FOREIGN PATENT DOCUMENTS

| | | |
|---|---|---|
| WO | 00/43316 | 7/2000 |
| WO | 01/53236 A1 | 7/2001 |

OTHER PUBLICATIONS

Lobo, CIT-1: A New Molecular Sieve with Intersecting Pores Bounded by 10- and 12-Rings, J. Am. Chem Soc., 1995, vol. 117, pp. 3766-3779.
Wright, Synthesis and structure of novel large-pore microporous magnesium-containing aluminophosphate (DAF-1), Chem. Commun., 1993, pp. 633-635.
Muncaster, An in Situ Microcrystal X-ray Diffraction Study of the Synthetic Aluminophosphate Zeotypes DAF-1 and CoAPSO-44, Chem. Mater, 1999, vol. 11, pp. 158-163.
Lewis, Experimental Charge Density Matching Approach to Zeolite Synthesis, Studies in Surface Science and Catalysis, 2004, vol. 154A, pp. 364-372.
Dorset, Douglas L., Crystal Structure of Zeolite MCM-68: A New Three-Dimensional Framework with Large Pores, J. Phys. Chem., B 2006, vol. 110, pp. 2045-2050.
Elangovan, A Comparative study of zeolites SSZ-33 and MCM-68 for hydrocarbon trap applications, Microporous and Mesoporous Materials, 96 2006, pp. 210-215.
Ernst, Characterization and Catalytic Evaluation of Zeolite MCM-68, Studies in Surface Science and Catalysis, 2004, vol. 154, pp. 2861-2868.
Koyama, A Multi-Dimensional Microporous Silicate That is Isomorphous to Zeolite MCM-68, Microporous Siliciates, Angew. Chem. Int. Ed. 2008, vol. 47, pp. 1042-4016.

* cited by examiner

*Primary Examiner* — Tam M Nguyen
(74) *Attorney, Agent, or Firm* — Maryann Maas

(57) ABSTRACT

Catalytic cracking processes such as fluidized catalytic cracking, naphtha cracking, and olefin cracking are catalyzed by the UZM-35 family of crystalline aluminosilicate zeolitic compositions represented by the empirical formula:

$$M_m^{n+}R_r^+Al_{(1-x)}E_xSi_yO_z$$

where M represents a combination of potassium and sodium exchangeable cations, R is a singly charged organoammonium cation such as the dimethyldipropylammonium cation and E is a framework element such as gallium. These UZM-35 zeolitic compositions are active and selective in the catalytic cracking of hydrocarbons.

20 Claims, No Drawings

PROCESS FOR CATALYTIC CRACKING OF HYDROCARBONS USING UZM-35

FIELD OF THE INVENTION

The present invention relates to the use of zeolite UZM-35 in a process of catalytic cracking organic compounds. The zeolite UZM-35 may be present in the catalytic cracking catalyst as the sole zeolite component, or may be in a UZM-35 composition with additional zeolites such as a MFI zeolite and an ERI zeolite. The zeolite UZM-35 or UZM-35 composition may be present in the catalyst as synthesized (unmodified zeolite(s)) or as modified zeolite(s). The catalyst may take one of several forms, including for example, a solid fluidizable catalyst, a spherical oil-dropped catalyst or an extruded catalyst.

BACKGROUND OF THE INVENTION

Zeolites are crystalline aluminosilicate compositions which are microporous and which are formed from corner sharing $AlO_2$ and $SiO_2$ tetrahedra. Numerous zeolites, both naturally occurring and synthetically prepared, are used in various industrial processes. Synthetic zeolites are prepared via hydrothermal synthesis employing suitable sources of Si, Al and structure directing agents such as alkali metals, alkaline earth metals, amines, or organoammonium cations. The structure directing agents reside in the pores of the zeolite and are largely responsible for the particular structure that is ultimately formed. These species balance the framework charge associated with aluminum and can also serve as space fillers. Zeolites are characterized by having pore openings of uniform dimensions, having a significant ion exchange capacity, and being capable of reversibly desorbing an adsorbed phase which is dispersed throughout the internal voids of the crystal without significantly displacing any atoms which make up the permanent zeolite crystal structure. Topological zeolite structure are described in *Atlas of Zeolite Framework Types*, which is maintained by the International Zeolite Association Structure Commission at http://www.iza-structure.org/databases/. Zeolites can be used as catalysts for hydrocarbon conversion reactions, which can take place on outside surfaces as well as on internal surfaces within the pore.

Catalytic cracking processes are used in several areas of the refinery. Fluidized catalytic cracking (FCC) converts heavy feeds to lighter products including diesel, gasoline and light olefins. FCC was traditionally used for conversion of heavy feeds such as VGO (vacuum gas oil) to gasoline and diesel but has recently been extended to the co-production of propylene. This process typically uses at least one of a 12-membered-ring and or a 10-membered-ring zeolite such as FAU or MFI to catalyze the conversion of heavy feeds with high selectivity to gasoline and/or propylene. Naphtha cracking has been heavily studied and converts naphtha feeds with high selectivity to propylene using 12-membered ring or 10-membered ring zeolites. Olefin cracking converts olefinic feeds such as butenes or pentenes with high selectivity to propylene using 10-membered-ring zeolite catalysts such as MFI and MEL. In all these catalytic cracking processes, new catalysts are continuously needed with high overall conversion of the feedstock and good selectivity to propylene.

Especially advantageous would be a commercially utilizable catalyst containing 12-membered rings and 10-membered rings in the same 3-dimensional structure. Commercial utility is typically seen in aluminosilicate structures which are synthesized in hydroxide media with readily available structure directing agents. Zeolites which contain both 12-membered and 10-membered rings in 3-dimensional structures belong to the CON, DFO, IWR, IWW and MSE structure types. The synthesis of CIT-1, a zeolite of the CON structure type, is described in U.S. Pat. No. 5,512,267 and in J. Am. Chem. Soc. 1995, 117, 3766-79 as a borosilicate form. After synthesis, a subsequent step can be undertaken to allow substitution of Al for B. The zeolites SSZ-26 and SSZ-33, also of the CON structure type are described in U.S. Pat. No. 4,910,006 and U.S. Pat. No. 4,963,337 respectively. SSZ-33 is also described as a borosilicate. All 3 members of the CON structure type use very complicated, difficult to synthesize structure directing agents which make commercial utilization difficult. The known member of the DFO structure type is DAF-1 which is described as an aluminophosphate in Chem. Commun. 1993, 633-35 and in Chem. Mater. 1999, 11, 158-63. Zeolites from the IWR and IWW structure types are synthesized only in hydrofluoric acid containing synthesis routes, making commercial utilization difficult.

One particular zeolite of the MSE structure type, designated MCM-68, was disclosed by Calabro et al. in 1999 (U.S. Pat. No. 6,049,018). This patent describes the synthesis of MCM-68 from dication directing agents, N,N,N',N'-tetraalkylbicyclo[2.2.2]oct-7-ene-2R,3S:5R,6S-dipyrrolidinium dication, and N,N,N',N'-tetraalkylbicyclo[2.2.2]octane-2R,3S:5R,6S-dipyrrolidinium dication. MCM-68 was found to have at least one channel system in which each channel is defined by a 12-membered ring of tetrahedrally coordinated atoms and at least two further independent channel systems in which each channel is defined by a 10-membered ring of tetrahedrally coordinated atoms wherein the number of unique 10-membered ring channels is twice the number of 12-membered ring channels.

Applicants have successfully prepared a new family of materials designated UZM-35. The topology of the materials is similar to that observed for MCM-68. The materials are prepared via the use of simple, commercially available structure directing agents, such as dimethyldipropylammonium hydroxide, in concert with small amounts of $K^+$ and $Na^+$ together using the Charge Density Mismatch Approach to zeolite synthesis (U.S. Pat. No. 7,578,993).

The UZM-35 family of materials is able to provide and maintain high conversion during catalytic cracking reactions and high selectivity to propylene due to its particular pore geometry and framework Si/Al ratio. The UZM-35 material contains significant amounts of Al in the tetrahedral framework, with the mole ratio of Si/Al ranging from about 2 to about 12. Al content in the framework is known to correspond to high activity in catalytic cracking processes.

Due to the unique structure of UZM-35, catalysts made from UZM-35 are able to show high conversion of n-heptane with good selectivity to olefins. In n-heptane cracking, UZM-35 converts greater than 70% of n-heptane at 500° C. with high selectivity of 34% to propylene with only 12% selectivity to light alkanes (C1, C2, C3). In comparison, with the same mass of zeolite, DHCD-4-CB (MFI based catalyst) converts 84% of the n-heptane feed with a selectivity to propylene of only 30%. Additionally, DHCD-4 has a selectivity of 15% to light alkanes under these conditions.

In the conversion of C4-olefins to propylene by catalytic cracking, UZM-35 catalysts are also effective. UZM-35 gives much higher conversion than the reference MFI catalyst with similar light olefin yields at equivalent conversion. For the reference MFI, a conversion of 55 wt-% is achieved at 580° C., 7 psig, 13.5 WHSV with selectivity of 65 wt-% to propylene. For UZM-35, 52 wt-% conversion is achieved at 520° C., 7 psig, 40 WHSV with a propylene selectivity of 63.5 wt-%. UZM-35 gives the beneficial property of running at much less harsh conditions for the same approximate light olefin yields.

SUMMARY OF THE INVENTION

The present invention relates to a process of catalytic cracking of hydrocarbons using a catalyst of the aluminosilicate zeolite designation UZM-35. The process comprises contacting the hydrocarbon with the UZM-35 at catalytic cracking conditions to give a catalytically cracked hydrocarbon product.

The UZM-35 is a microporous crystalline zeolite composition having a three-dimensional framework of at least $AlO_2$ and $SiO_2$ tetrahedral units and an empirical composition in the as synthesized and anhydrous basis expressed by an empirical formula of:

$$M_m^{+}R_r^{+}Al_{1-x}E_xSi_yO_z$$

where M represents a combination of potassium and sodium exchangeable cations, "m" is the mole ratio of M to (Al+E) and varies from about 0.05 to about 3, R is a singly charged organoammonium cation selected from the group consisting of dimethyldipropylammonium (DMDPA$^+$), dimethyldiisopropylammonium (DMDIP$^+$), choline, ethyltrimethylammonium (ETMA$^+$), diethyldimethylammonium (DEDMA$^+$), trimethylpropylammonium, trimethylbutylammonium, dimethyldiethanolammonium, tetraethylammonium (TEA$^+$), tetrapropylammonium (TPA$^+$), methyltripropylammonium, and mixtures thereof, "r" is the mole ratio of R to (Al+E) and has a value of about 0.25 to about 2.0, E is an element selected from the group consisting of gallium, iron, boron and mixtures thereof, "x" is the mole fraction of E and has a value from 0 to about 1.0, "y" is the mole ratio of Si to (Al+E) and varies from greater than 2 to about 12 and "z" is the mole ratio of O to (Al+E) and has a value determined by the equation:

$$z=(m+r+3+4\cdot y)/2$$

and is characterized in that it has the x-ray diffraction pattern having at least the d-spacings and intensities set forth in Table A

TABLE A

| 2θ | d(Å) | I/Io % |
|---|---|---|
| 6.45-6.8 | 13.7-13 | m |
| 6.75-7.13 | 13.1-12.4 | m-vs |
| 7.86-8.26 | 11.25-10.7 | m |
| 8.64-9.04 | 10.23-9.78 | m |
| 9.51-10.09 | 9.3-8.77 | m-vs |
| 10.62-11.23 | 8.33-7.88 | w-m |
| 13.4-14.22 | 6.61-6.23 | w-m |
| 14.76-15.55 | 6-5.7 | w |
| 17.63-18.37 | 5.03-4.83 | w |
| 19.17-19.91 | 4.63-4.46 | w-m |
| 19.64-20.56 | 4.52-4.32 | m |
| 20.18-21.05 | 4.4-4.22 | w-m |
| 20.7-21.57 | 4.29-4.12 | w-m |
| 21.36-22.28 | 4.16-3.99 | vs |
| 22.17-23.6 | 4.01-3.77 | m-s |
| 24.12-25.23 | 3.69-3.53 | w |
| 25.6-26.94 | 3.48-3.31 | m |
| 26.37-27.79 | 3.38-3.21 | m |
| 27.02-28.42 | 3.3-3.14 | m |
| 27.53-28.89 | 3.24-3.09 | m |
| 28.7-30.09 | 3.11-2.97 | m |
| 29.18-30.72 | 3.06-2.91 | w-m |
| 30.19-31.73 | 2.96-2.82 | m |
| 30.83-32.2 | 2.9-2.78 | w |
| 32.81-34.22 | 2.73-2.62 | w |
| 35.63-36.99 | 2.52-2.43 | w |
| 41.03-42.86 | 2.2-2.11 | w |
| 44.18-45.83 | 2.05-1.98 | w |
| 44.87-46.57 | 2.02-1.95 | w |
| 46.07-47.35 | 1.97-1.92 | w |
| 48.97-50.42 | 1.86-1.81 | w | and is thermally stable up to a temperature of greater than 400° C. in one embodiment and 600° C. in another embodiment. When using a the Rietveld refinement method described in J. Appl. Cryst. (1969) 2, 65-71) the x-ray diffraction pattern has at least the d-spacings and intensities set forth in Table A'

TABLE A'

| 2θ | d(Å) | I/Io % |
|---|---|---|
| 6.48-6.51 | 13.32-13.58 | m |
| 6.78-6.83 | 12.91-13.02 | m-s |
| 7.79-7.96 | 11.09-11.32 | m |
| 8.05-8.07 | 10.93-10.96 | m |
| 8.71-8.75 | 10.08-10.13 | m |
| 9.61-9.65 | 9.15-9.18 | m-s |
| 10.75-10.79 | 8.18-8.21 | w |
| 13.61-13.65 | 6.47-6.49 | w |
| 14.74-14.79 | 5.98-6 | w |
| 15.56-15.59 | 5.67-5.69 | w |
| 15.86-15.86 | 5.58-5.58 | w |
| 19.46-19.5 | 4.54-4.55 | m |
| 19.89-19.92 | 4.45-4.45 | m |
| 20.48-20.51 | 4.32-4.33 | m |
| 20.94-20.96 | 4.23-4.23 | m |
| 21.61-21.64 | 4.1-4.1 | vs |
| 21.79-21.81 | 4.07-4.07 | s |
| 22.39-22.45 | 3.95-3.96 | m |
| 22.93-22.98 | 3.86-3.87 | s-vs |
| 23.29-23.31 | 3.81-3.81 | m |
| 23.5-23.5 | 3.78-3.78 | m |
| 23.78-23.86 | 3.72-3.73 | m |
| 24.39-24.41 | 3.64-3.64 | w |
| 24.82-24.82 | 3.58-3.58 | w |
| 25.76-25.79 | 3.45-3.45 | w-m |
| 26.09-26.12 | 3.4-3.41 | m |
| 26.74-26.81 | 3.32-3.33 | m |
| 27.14-27.14 | 3.28-3.28 | m |
| 27.42-27.46 | 3.24-3.249 | m |
| 27.69-27.69 | 3.21-3.21 | m |
| 28.02-28.06 | 3.17-3.18 | m |
| 29.1-29.15 | 3.06-3.06 | m |
| 29.54-29.61 | 3.01-3.02 | w |
| 29.75-29.86 | 2.98-2.99 | w |
| 30.12-30.14 | 2.96-2.96 | m |
| 30.73-30.79 | 2.9-2.9 | m |
| 31.26-31.27 | 2.85-2.85 | w |
| 31.47-31.47 | 2.83-2.83 | w |
| 33.19-33.25 | 2.69-2.69 | w |
| 34.34-34.48 | 2.59-2.6 | w |
| 34.76-34.76 | 2.57-2.57 | w |
| 35.18-35.2 | 2.54-2.54 | w |
| 35.57-35.59 | 2.51-2.52 | w |
| 36.02-36.04 | 2.48-2.49 | w |
| 41.65-41.71 | 2.16-2.16 | w |
| 44.57-44.61 | 2.02-2.03 | w |
| 47.48-47.58 | 1.9-1.91 | w |
| 49.53-49.59 | 1.83-1.83 | w |

The crystalline microporous zeolite composition described above may be synthesized by forming a reaction mixture containing reactive sources of M, R, Al, Si and optionally E and heating the reaction mixture at a temperature of about 150° C. to about 200° C., or about 165° C. to about 185° C., for a time sufficient to form the zeolite composition, the reaction mixture having a composition expressed in terms of mole ratios of the oxides of:

$$aM_2O:bR_{2/p}O:1-cAl_2O_3:cE_2O_3:dSiO_2:eH_2O$$

where "a" has a value of about 0.05 to about 1.25, "b" has a value of about 1.5 to about 40, "p" is the weighted average valance of R and varies from 1 to about 2, "c" has a value of 0 to about 1.0, "d" has a value of about 4 to about 40, "e" has a value of about 25 to about 4000.

DETAILED DESCRIPTION OF THE INVENTION

Applicants have prepared an aluminosilicate zeolite composition, which has been designated UZM-35 composition whose main component has a topological structure, which is related to MSE as described in *Atlas of Zeolite Framework Types*, maintained by the International Zeolite Association Structure Commission at http://www.iza-structure.org/databases/. As is shown in U.S. Ser. No. 12/241,302 in detail, UZM-35 is different from MCM-68 in a number of its characteristics. The instant microporous crystalline zeolitic composition, UZM-35, has an empirical composition in the as-synthesized form and on an anhydrous basis expressed by the empirical formula:

$$M_m^+R_r^+Al_{1-x}E_xSi_yO_z$$

where M represents a combination of potassium and sodium exchangeable cations. R is a singly charged organoammonium cation, examples of which include but are not limited to the dimethyldipropylammonium cation (DMDPA$^+$), dimethyldiisopropylammonium (DMDIP$^+$), choline [(CH$_3$)$_3$N(CH$_2$)$_2$OH]$^+$, ETMA$^+$, DEDMA$^+$, trimethylpropylammonium, trimethylbutylammonium, dimethyldiethanolammonium, methyltripropylammonium, TEA$^+$, TPA$^+$ and mixtures thereof and "r" is the mole ratio of R to (Al+E) and varies from about 0.25 to about 2.0 while "m" is the mole ratio of M to (Al+E) and varies from about 0.05 to about 3. The mole ratio of silicon to (Al+E) is represented by "y" which varies from about 2 to about 30. E is an element which is tetrahedrally coordinated, is present in the framework and is selected from the group consisting of gallium, iron and boron. The mole fraction of E is represented by "x" and has a value from 0 to about 1.0, while "z" is the mole ratio of O to (Al+E) and is given by the equation:

$$z=(m \cdot n+r+3+4 \cdot y)/2.$$

Where M is only one metal, then the weighted average valence is the valence of that one metal, i.e. +1 or +2. However, when more than one M metal is present, the total amount of:
and the weighted average valence "n" is given by the equation:

$$n = \frac{m_1 \cdot n_1 + m_2 \cdot n_2 + m_3 \cdot n_3 + \ldots}{m_1 + m_2 + m_3 \ldots}$$

The microporous crystalline zeolitic composition, UZM-35, is prepared by a hydrothermal crystallization of a reaction mixture prepared by combining reactive sources of M, R, aluminum, silicon and optionally E. The sources of aluminum include but are not limited to aluminum alkoxides, precipitated aluminas, aluminum metal, aluminum salts and alumina sols. Specific examples of aluminum alkoxides include, but are not limited to aluminum ortho sec-butoxide and aluminum ortho isopropoxide. Sources of silica include but are not limited to tetraethylorthosilicate, colloidal silica, precipitated silica and alkali silicates. Sources of the E elements include but are not limited to alkali borates, boric acid, precipitated gallium oxyhydroxide, gallium sulfate, ferric sulfate, and ferric chloride. Sources of the M metals, potassium and sodium, include the halide salts, nitrate salts, acetate salts, and hydroxides of the respective alkali metals. R is an organoammonium cation selected from the group consisting of dimethyldipropylammonium, choline, ETMA, DEDMA, TEA, TPA, trimethylpropylammonium, trimethylbutylammonium, dimethyldiethanolammonium and mixtures thereof, and the sources include the hydroxide, chloride, bromide, iodide and fluoride compounds. Specific examples include without limitation dimethyldipropylammonium hydroxide, dimethyldipropylammonium chloride, dimethyldipropylammonium bromide, dimethyldiisopropylammonium hydroxide, dimethyldiisopropylammonium chloride, dimethyldiisopropylammonium bromide, ethyltrimethylammonium hydroxide, diethyldimethylammonium hydroxide, tetraethylammonium hydroxide, tetrapropylammonium hydroxide, and tetrapropylammonium chloride.

Note that during synthesis, the metal M is +1 valance, specifically potassium and sodium. However, in an alternative embodiment, the composition may undergo additional ion exchange steps post synthesis to provide a material with one or more metals, M, having a +2 valence.

The reaction mixture containing reactive sources of the desired components can be described in terms of molar ratios of the oxides by the formula:

$$aM_2O:bR_{2/p}O:1-cAl_2O_3:cE_2O_3:dSiO_2:eH_2O$$

where "a" varies from about 0.05 to about 1.25, "b" varies from about 1.5 to about 40, "c" varies from 0 to 1.0, "d" varies from about 4 to about 40, "e" varies from about 25 to about 4000, and "p" is the weighted average valence of R and varies from 1 to about 2. If alkoxides are used, it is preferred to include a distillation or evaporative step to remove the alcohol hydrolysis products. The reaction mixture is now reacted at a temperature of about 150° C. to about 200° C., about 165° C. to about 185° C., or about 170° C. to about 180° C., for a period of about 1 day to about 3 weeks and preferably for a time of about 5 days to about 12 days in a sealed reaction vessel under autogenous pressure. After crystallization is complete, the solid product is isolated from the heterogeneous mixture by means such as filtration or centrifugation, and then washed with deionized water and dried in air at ambient temperature up to about 100° C. It should be pointed out that UZM-35 seeds can optionally be added to the reaction mixture in order to accelerate the formation of the zeolite.

A preferred synthetic approach to make UZM-35 utilizes the charge density mismatch concept, which is disclosed in U.S. Pat. No. 7,578,993 and *Studies in Surface Science and Catalysis*, (2004), Vol. 154A, 364-372. The method disclosed in U.S. Pat. No. 7,578,993 employs quaternary ammonium hydroxides to solubilize aluminosilicate species, while crystallization inducing agents such as alkali and alkaline earth metals and more highly charged organoammonium cations are often introduced in a separate step. Once some UZM-35 seeds have been generated using this approach, the seeds can be used in a single step synthesis of UZM-35, using, for example, a combination of dimethyldipropylammonium hydroxide and the alkali cations. The use of commercially available dimethyldipropylammonium hydroxide to prepare UZM-35 offers a great economic advantage over the structure directing agents previously employed (N,N,N',N'-tetraalkylbicyclo[2.2.2]oct-7-ene-2R,3S:5R,6S-dipyrrolidinium dication, and N,N,N',N'-tetraalkylbicyclo[2.2.2]octane-2R,3S:5R,6S-dipyrrolidinium dication) to prepare aluminosilicates with the MSE topology. Additionally, dimethyldipropyl ammonium hydroxide can be employed as the hydroxide or the chloride in concert with other inexpensive organoammonium hydroxides using the charge density mismatch concept to reduce costs even further.

The UZM-35 aluminosilicate zeolitic composition, which is obtained from the above-described process, is characterized by the x-ray diffraction pattern, having at least the d-spacings and relative intensities set forth in Table A below.

TABLE A

| 2θ | d(Å) | I/Io % |
|---|---|---|
| 6.45-6.8 | 13.7-13 | m |
| 6.75-7.13 | 13.1-12.4 | m-vs |
| 7.86-8.26 | 11.25-10.7 | m |
| 8.64-9.04 | 10.23-9.78 | m |
| 9.51-10.09 | 9.3-8.77 | m-vs |
| 10.62-11.23 | 8.33-7.88 | w-m |
| 13.4-14.22 | 6.61-6.23 | w-m |
| 14.76-15.55 | 6-5.7 | w |
| 17.63-18.37 | 5.03-4.83 | w |
| 19.17-19.91 | 4.63-4.46 | w-m |
| 19.64-20.56 | 4.52-4.32 | m |
| 20.18-21.05 | 4.4-4.22 | w-m |
| 20.7-21.57 | 4.29-4.12 | w-m |
| 21.36-22.28 | 4.16-3.99 | vs |
| 22.17-23.6 | 4.01-3.77 | m-s |
| 24.12-25.23 | 3.69-3.53 | w |
| 25.6-26.94 | 3.48-3.31 | m |
| 26.37-27.79 | 3.38-3.21 | m |
| 27.02-28.42 | 3.3-3.14 | m |
| 27.53-28.89 | 3.24-3.09 | m |
| 28.7-30.09 | 3.11-2.97 | m |
| 29.18-30.72 | 3.06-2.91 | w-m |
| 30.19-31.73 | 2.96-2.82 | m |
| 30.83-32.2 | 2.9-2.78 | w |
| 32.81-34.22 | 2.73-2.62 | w |
| 35.63-36.99 | 2.52-2.43 | w |
| 41.03-42.86 | 2.2-2.11 | w |
| 44.18-45.83 | 2.05-1.98 | w |
| 44.87-46.57 | 2.02-1.95 | w |
| 46.07-47.35 | 1.97-1.92 | w |
| 48.97-50.42 | 1.86-1.81 | w |

As will be shown in detail in the examples, the UZM-35 material is thermally and catalytically stable up to a temperature of at least 400° C. and in another embodiment, up to about 600° C. The UZM-35 composition as synthesized comprises a MSE topology zeolite, a MFI topology zeolite and an ERI topology zeolite. Typically, the amount of MSE zeolite in the composition will vary from about 55 wt % to about 75 wt. % or from about 55 wt-% to about 90 wt.-%. The amount of MFI zeolite varies from about 20 wt-% to about 35 wt-% of the composition or from about 10 wt-% to about 35 wt.-%, and the amount of ERI zeolite varies from about 3 wt-% to about 9 wt-% of the composition or from about 3 wt-% to about 10 wt.-%. Of course, the sum of the amount of the three zeolites, absent any other impurities, adds up to 100 wt % of the composition. When using a the Rietveld refinement method described in J. Appl. Cryst. (1969) 2, 65-71) the x-ray diffraction pattern has at least the d-spacing's and intensities set forth in Table A':

TABLE A'

| 2θ | d(Å) | I/Io % |
|---|---|---|
| 6.48-6.51 | 13.32-13.58 | m |
| 6.78-6.83 | 12.91-13.02 | m-s |
| 7.79-7.96 | 11.09-11.32 | m |
| 8.05-8.07 | 10.93-10.96 | m |
| 8.71-8.75 | 10.08-10.13 | m |
| 9.61-9.65 | 9.15-9.18 | m-s |
| 10.75-10.79 | 8.18-8.21 | w |
| 13.61-13.65 | 6.47-6.49 | w |
| 14.74-14.79 | 5.98-6 | w |
| 15.56-15.59 | 5.67-5.69 | w |
| 15.86-15.86 | 5.58-5.58 | w |
| 19.46-19.5 | 4.54-4.55 | m |
| 19.89-19.92 | 4.45-4.45 | m |
| 20.48-20.51 | 4.32-4.33 | m |
| 20.94-20.96 | 4.23-4.23 | m |
| 21.61-21.64 | 4.1-4.1 | vs |
| 21.79-21.81 | 4.07-4.07 | s |
| 22.39-22.45 | 3.95-3.96 | m |
| 22.93-22.98 | 3.86-3.87 | s-vs |
| 23.29-23.31 | 3.81-3.81 | m |
| 23.5-23.5 | 3.78-3.78 | m |
| 23.78-23.86 | 3.72-3.73 | m |
| 24.39-24.41 | 3.64-3.64 | w |
| 24.82-24.82 | 3.58-3.58 | w |
| 25.76-25.79 | 3.45-3.45 | w-m |
| 26.09-26.12 | 3.4-3.41 | m |
| 26.74-26.81 | 3.32-3.33 | m |
| 27.14-27.14 | 3.28-3.28 | m |
| 27.42-27.46 | 3.24-3.249 | m |
| 27.69-27.69 | 3.21-3.21 | m |
| 28.02-28.06 | 3.17-3.18 | m |
| 29.1-29.15 | 3.06-3.06 | m |
| 29.54-29.61 | 3.01-3.02 | w |
| 29.75-29.86 | 2.98-2.99 | w |
| 30.12-30.14 | 2.96-2.96 | m |
| 30.73-30.79 | 2.9-2.9 | m |
| 31.26-31.27 | 2.85-2.85 | w |
| 31.47-31.47 | 2.83-2.83 | w |
| 33.19-33.25 | 2.69-2.69 | w |
| 34.34-34.48 | 2.59-2.6 | w |
| 34.76-34.76 | 2.57-2.57 | w |
| 35.18-35.2 | 2.54-2.54 | w |
| 35.57-35.59 | 2.51-2.52 | w |
| 36.02-36.04 | 2.48-2.49 | w |
| 41.65-41.71 | 2.16-2.16 | w |
| 44.57-44.61 | 2.02-2.03 | w |
| 47.48-47.58 | 1.9-1.91 | w |
| 49.53-49.59 | 1.83-1.83 | w |

One advantage of the UZM-35 material is that it may be used as a catalytic cracking catalyst without having to remove the potassium from the as synthesized material. In other words, the potassium does not need to be removed in order for the catalytic cracking catalyst to be active. The catalyst, in its catalytically active state, may contain molar ratios of potassium to alumina of less than 0.90.

As synthesized, the UZM-35 material will contain some of the exchangeable or charge balancing cations in its pores. These exchangeable cations can be exchanged for other cations, or in the case of organic cations, they can be removed by heating under controlled conditions. Because the UZM-35 composition comprises large pore zeolite(s), it is also possible to remove some organic cations directly by ion exchange. The UZM-35 composition may be modified in many ways to tailor it for use in a particular application. Modifications include calcination, ion-exchange, steaming, various acid extractions, ammonium hexafluorosilicate treatment, or any combination thereof, as outlined for the case of UZM-4M in U.S. Pat. No. 6,776,975 B1 which is incorporated by reference in its entirety. Properties that are modified include porosity, adsorption, Si/Al mole ratio, acidity, thermal stability, and the like.

The UZM-35 composition as outlined above or a modification thereof, is used as a catalyst or catalyst support in various hydrocarbon catalytic cracking processes. The catalyst may contain from about 30 or 40 to about 80 mass % of the UZM-35 composition. Catalytic cracking of hydrocarbons are processes well known in the art and include for example, fluidized catalytic cracking (FCC), naphtha cracking, and olefin cracking. Cracking is a process used for breaking complex organic molecules such as heavy hydrocarbons into simpler molecules achieved by the cleaving of carbon-carbon bonds in the precursors, typically in the presence of a catalyst. The catalytic cracking process involves the presence of acid catalysts (usually solid acids such as silica-alumina and zeolites) which promote a breakage of bonds yielding olefins and paraffins of smaller molecular weight. Additionally, intra- and intermolecular hydrogen transfer or hydride transfer as well as reactions such as oligomerization and aromatization occur. The rate of cracking and the nature of the end products are dependent on the conditions under which the process is carried out, such as the temperature, the pressure, the amount of time the catalyst and feedstock are in contact and the nature of any catalysts used.

Fluid catalytic cracking (FCC) is one type of catalytic cracking process that is widely used. The process typically employs a powdered catalyst having the particles suspended in a rising flow of feed hydrocarbons to form a fluidized bed. Zeolite-based catalysts are commonly used as are composite catalysts which contain zeolites, silica-aluminas, alumina and other binders. In representative processes, cracking takes place in a riser, which is a vertical or upward sloped pipe.

A pre-heated feed (e.g., a vacuum gas oil) may be sprayed into the base of the riser via feed nozzles where it contacts hot fluidized catalyst at a temperature between about 400° C. and about 800° C. The feed is vaporized on contact with the catalyst and the cracking occurs converting the high molecular weight oil into lighter components including liquefied petroleum gas (LPG), gasoline, and a distillate. The catalyst-feed mixture flows upward through the riser for a short period (few seconds) and then the mixture is separated in cyclones. The hydrocarbons thus separated from the catalyst are directed to a fractionator for separation into LPG, gasoline, diesel, kerosene, jet fuel, and other possible fractions.

While going through the riser, the cracking catalyst is deactivated because the process is accompanied by formation of deposit coke on the catalyst particles. So contaminated catalyst is separated from the cracked hydrocarbon vapors and is further treated with steam to remove hydrocarbons remaining in the catalyst's pores. The catalyst is then directed into a regenerator where the coke is burned off the catalyst particles surface, thus restoring the catalyst's activity and providing the necessary heat for the next reaction cycle. The process of cracking is endothermic. The regenerated catalyst is then used in the new cycle. New catalysts for catalytic cracking processes such as FCC should therefore be capable of regeneration. The UZM-35 composition, in one embodiment, is stable with regard to regeneration.

Catalytic cracking processes are carried out with the UZM-35 composition using feedstocks such as gas oils, heavy naphtha, cycle oils, deasphalted crude oil residua, Fischer-Tropsch wax, slack wax, hydrotreated products of the foregoing and combinations thereof, with gasoline being the typically desired product. Temperature conditions of from about 400° C. to about 800° C., pressure conditions of from about 0 to about 688 kPa g (about 0 to 100 psig) and contact times of from about 0.1 seconds to about 1 hour are suitable. Temperature conditions of from about 450° C. to about 700° C., pressure conditions of from about 0 to about 344 kPa g (about 0 to 50 psig) and contact times of from about 0.1 seconds to about several minutes are often preferred. The preferred conditions are determined based on the hydrocarbon feedstock being cracked and the cracked products desired.

Naphtha cracking processes are preferably carried out with the UZM-35 composition using a naphtha feedstock, such as, but not limited to, straight-run naphtha, Coker naphtha, Visbreaker naphtha, FCC naphtha, and Catalytic Polymerization naphtha (Cat Poly naphtha) which are catalytically cracked to light olefins such as ethylene and propylene. The naphtha is contacted with the UZM-35 composition catalyst in, for example, a fluidized catalytic cracking (FCC) type reactor. The choice of reactor can be any type of reactor for intimately mixing the naphtha feedstream with the catalyst. Reactors of this type are well known to those skilled in the art. A fluidized reactor usable in this invention is described in U.S. Pat. No. 6,183,699, which is incorporated by reference in its entirety.

Alternatively, reactor types such as moving bed reactors with continuous catalyst regeneration, or fixed bed reactors with periodic catalyst regeneration by pressure swing or temperature swing may be utilized to contact the hydrocarbon feed with the UZM-35 zeolite catalyst. New catalysts for catalytic cracking processes such as naphtha cracking should therefore be capable of regeneration. The UZM-35 composition, in one embodiment, is stable with regard to regeneration.

The naphtha cracking reactions can be carried out between a temperature of about 400° C. to about 700° C. The cracking process may be carried out using pressure conditions of from about 0 to about 688 kPa g (about 0 to 100 psig) and a contact time from about 0.1 seconds to about 1 hour and preferably from about 0.1 seconds to about 0.1 hour. The longer contact times are used at lower temperatures while shorter times are used at higher temperatures, assuming all other process variables are equal.

Olefin cracking processes are preferably carried out with the UZM-35 composition using feedstocks such as a mixed olefin stream comprising $C_4$ or $C_5$ to $C_{10}$ olefins, with ethylene, propylene, and butene being the principal desired products. In some applications, the butene may be recycled to be cracked as well. The operation of an olefin cracking reactor is at a temperature from 400° C. to 650° C., and preferably between 500° C. to 600° C. The pressure for the olefin cracking reactor during operation is between 0 kPa to 344 kPa, with a preferred operating pressure between 10 kPa to 200 kPa for the olefin partial pressure. The contact time for the olefin cracking process is from about 0.1 seconds to about 1 hour.

The $C_4$ or $C_5$ to $C_{10}$ olefin feedstock is passed over a UZM-35 catalyst bed to crack the olefins into smaller molecules. The cracking process generates some coking on the catalyst, and over time the catalyst activity is reduced due to plugging of the catalyst pores with coke. The catalyst may be regenerated though oxidizing the coke and removing it as gas comprising primarily $N_2$, $H_2O$, CO and $CO_2$. The catalyst in the reactors may be regenerated periodically, and therefore the process may swing between multiple reactors on a frequent basis. Alternatively, reactor types such as moving or fluidized bed reactors with continuous catalyst regeneration may be utilized to contact the hydrocarbon feed with the UZM-35 composition catalyst. New catalysts for catalytic cracking processes such as olefin cracking should therefore be capable of regeneration. The UZM-35 composition, in one embodiment, is stable with regard to regeneration.

Additional zeolites may be combined with the UZM-35 composition. For example, one or more zeolites of the FAU or MFI structure types may be composited with the UZM-35 composition. The weight ratio of UZM-35 to the one or more zeolites of the FAU or MFI structure types may be from about 0.01 to about 50. In other applications, the weight ratio of UZM-35 to the one or more zeolites of the FAU or MFI structure types may be from about 0.01 to about 1.

The reaction zone effluent is normally removed from the catalyst bed, subjected to partial condensation and vapor-liquid separation and then fractionated to recover the various components thereof. The hydrogen, and if desired some or all of the unconverted heavier materials, are recycled to the reactor. Alternatively, a two-stage flow may be employed with the unconverted material being passed into a second reactor.

The following examples are presented in illustration of this invention and are not intended as undue limitations on the generally broad scope of the invention as set out in the appended claims.

The structure of the UZM-35 zeolitic composition of this invention was determined by x-ray analysis. The x-ray patterns presented in the following examples were obtained using standard x-ray powder diffraction techniques. The radiation source was a high-intensity, x-ray tube operated at 45 kV and 35 ma. The diffraction pattern from the copper K-alpha radiation was obtained by appropriate computer based techniques. Flat compressed powder samples were continuously scanned at 2° to 56° (2θ). Interplanar spacings (d) in Angstrom units were obtained from the position of the diffraction peaks expressed as θ where θ is the Bragg angle as observed from digitized data. Intensities were determined from the integrated area of diffraction peaks after subtracting background, "$I_o$" being the intensity of the strongest line or peak, and "I" being the intensity of each of the other peaks.

As will be understood by those skilled in the art the determination of the parameter 2θ is subject to both human and mechanical error, which in combination can impose an uncertainty of about ±0.4° on each reported value of 2θ. This uncertainty is, of course, also manifested in the reported values of the d-spacings, which are calculated from the 2θ values. This imprecision is general throughout the art and is not sufficient to preclude the differentiation of the present crystalline materials from each other and from the compositions of the prior art. In some of the x-ray patterns reported, the relative intensities of the d-spacings are indicated by the notations vs, s, m, and w which represent very strong, strong, medium, and weak, respectively. In terms of $100 \times I/I_o$, the above designations are defined as:

$$w=0-15; m=15-60; s=60-80 \text{ and } vs=80-100$$

Examples 7 and 8 are synthesis examples that employed the x-ray diffraction technique known as the Rietveld refinement method, described in J. Appl. Cryst. (1969) 2, 65-71.

In certain instances, the purity of a synthesized product may be assessed with reference to its x-ray powder diffraction pattern. Thus, for example, if a sample is stated to be pure, it is intended only that the x-ray pattern of the sample is free of lines attributable to crystalline impurities, not that there are no amorphous materials present.

In order to more fully illustrate the invention, the following examples are set forth. It is to be understood that the examples are only by way of illustration and are not intended as an undue limitation on the broad scope of the invention as set forth in the appended claims.

Example 1

An aluminosilicate reaction solution was prepared by first mixing 27.17 g of aluminum hydroxide (27.78 mass-% Al) and 1053.58 g dimethyldipropylammonium hydroxide (18.8 mass-% solution), while stirring vigorously. After thorough mixing, 505.96 g Ludox™ AS-40 (40 mass-% $SiO_2$) was added. The reaction mixture was homogenized for an additional hour with a high speed mechanical stirrer, sealed in a Teflon bottle, and placed in an oven overnight at 100° C. Analysis showed the aluminosilicate solution contained 6.16 wt. % Si and 0.67 wt. % Al (Si/Al molar ratio of 8.83).

A 1200 g portion of the above aluminosilicate solution was continuously stirred. A composite aqueous solution containing 28.56 g of KOH and 3.6 g of NaOH dissolved in 150 g distilled water, was added, drop-wise, to the aluminosilicate solution. After the addition was completed, the resulting reaction mixture was homogenized for 1 hour, transferred to a 2000 ml Parr stainless steel autoclave which was heated to 175° C. and maintained at that temperature for 216 hrs. The solid product was recovered by centrifugation, washed with de-ionized water, and dried at 100° C.

The solid product was recovered by centrifugation, washed with de-ionized water and dried at 95° C. The product was identified as UZM-35 by xrd. Representative diffraction lines observed for the product are shown in Table 1. The product composition was determined by elemental analysis to consist of the following mole ratios: Si/Al=7.92, Na/Al=0.1, K/Al=0.48.

TABLE 1

| 2θ | d(Å) | $I/I_o$ % |
|---|---|---|
| 6.65 | 13.26 | m |
| 6.95 | 12.69 | m |
| 8.10 | 10.90 | m |
| 8.87 | 9.95 | m |
| 9.76 | 9.05 | m |
| 10.83 | 8.13 | w |
| 13.76 | 6.43 | w |
| 15.22 | 5.81 | w |
| 18.00 | 4.92 | w |
| 19.46 | 4.55 | m |
| 19.62 | 4.52 | m |
| 20.06 | 4.42 | m |
| 20.63 | 4.3 | m |
| 21.1 | 4.20 | m |
| 21.76 | 4.08 | vs |
| 21.92 | 4.05 | m |
| 22.07 | 4.03 | m |
| 22.55 | 3.93 | m |
| 22.73 | 3.90 | m |
| 23.08 | 3.85 | s |
| 23.42 | 3.79 | m |
| 23.51 | 3.77 | m |
| 24.04 | 3.69 | m |
| 24.53 | 3.62 | w |
| 25.9 | 3.43 | m |
| 25.99 | 3.42 | w |
| 26.27 | 3.38 | m |
| 26.92 | 3.3 | m |
| 27.57 | 3.23 | m |
| 27.76 | 3.21 | m |
| 28.17 | 3.16 | m |
| 28.86 | 3.09 | w |
| 29.27 | 3.04 | m |
| 29.72 | 3.00 | w |
| 30.26 | 2.95 | w |
| 30.91 | 2.88 | m |
| 31.38 | 2.84 | w |
| 33.61 | 2.68 | w |
| 34.65 | 2.58 | w |
| 35.43 | 2.53 | w |
| 36.18 | 2.48 | w |
| 41.77 | 2.16 | w |
| 44.7 | 2.02 | w |
| 45.32 | 1.99 | w |
| 45.63 | 1.98 | w |
| 46.55 | 1.94 | w |
| 47.62 | 1.90 | w |
| 47.94 | 1.89 | w |
| 49.70 | 1.83 | w |
| 51.06 | 1.78 | w |

Example 2

The UZM-35 of example 1 was calcined at 540 C for 10 hours under nitrogen and then under air. The UZM-35 was then ammonium ion exchanged to exchange Na or K cations for $NH_4$. The UzM-35 was ammonium ion-exchanged by contacting 500 mL of 1 M NH4NHO3 solution with 40 g UZM-35 at 80 C and stirring for 1 hour, filtered and washed. The procedure was repeated three times.

Example 3

The UZM-35 of Example 2 was then calcined at 550° C. in air for 2 h to convert $NH_4^+$ to $H^+$ by loss of ammonia.

Example 4

Alternatively, the ammonium exchange was performed first followed by calcination to remove the template and exchange $Na^+$ or $K^+$ for $NH4^+$. The UZM-35 of example 1 was ammonium ion-exchanged by contacting 500 mL of 1M $NH_4NO_3$ solution with 30 g UZM-35 at 80° C. and stirring for 1 h. The sample was calcined at 540° C. for 10 hrs under nitrogen and then air. A second ion exchange was carried out by contacting 500 mL of 1M $NH_4NO_3$ solution with 22 g UZM-35 at 80° C. and stirring for 1 h.

Comparative Example 5

A sample of H-MFI zeolite, bound 66/34 with $AlPO_4$ was obtained. The $SiO_2/Al_2O_3$ mole ratio of this material was 38.

Comparative Example 6

A sample of H-MFI zeolite, bound 80/20 with $SiO_2$ was obtained. This catalyst had been calcined and steamed prior to use. The $SiO_2/Al_2O_3$ ratio was about 500.

Prior to catalytic use, the $H^+$ form of UZM-35 was pressed and meshed to 20-40 mesh. For n-heptane cracking tests, 250 mg of zeolite was loaded into the reactor and a n-heptane saturated $N_2$ stream contacted the catalyst at 125 mL/min at atmospheric pressure. For catalysts which were tested as bound catalysts, 250 mg of zeolite was used. That is, for catalysts composed of 100% zeolite, 250 mg of catalyst was used, but for catalysts that contained 50% zeolite, 500 mg of catalyst was used. Results of the n-heptane cracking tests are shown in Table 2.

TABLE 2

| Catalyst | Temperature (° C.) | Conversion (wt %) | Light Paraffin Selectivity | Ethylene Selectivity | Propylene Selectivity | Butene Selectivity | Heavies Selectivity |
|---|---|---|---|---|---|---|---|
| Example 2 UZM-35 | 500 | 72 | 30 | 9 | 34 | 16 | 11 |
| Example 2 UZM-35 | 550 | 88 | 22 | 12 | 37 | 17 | 12 |
| Example 2 UZM-35 | 625 | 98 | 17.5 | 18.5 | 36.5 | 13.5 | 14 |
| Example 3 UZM-35 | 500 | 73 | 31 | 9 | 34 | 16 | 10 |
| Example 3 UZM-35 | 550 | 89 | 23 | 12 | 37 | 17 | 11 |
| Example 3 UZM-35 | 625 | 98 | 18 | 18 | 36.5 | 14 | 13.5 |
| Example 4 UZM-35 | 500 | 70 | 31 | 9 | 34 | 16 | 10 |
| Example 4 UZM-35 | 550 | 86.5 | 23 | 12 | 37 | 17 | 11 |
| Example 4 UZM-35 | 625 | 97 | 18 | 18 | 36.5 | 14 | 13.5 |
| Example 5 MFI | 500 | 84 | 29 | 13 | 31 | 13 | 14 |
| Example 5 MFI | 550 | 98 | 24 | 17.5 | 30 | 10 | 18.5 |
| Example 5 MFI | 625 | 100 | 17 | 27 | 25.5 | 3 | 27.5 |

Following the n-heptane cracking tests, the UZM-35 catalysts were unloaded from the reactor and found to have changed from a white color to black, indicating the presence of carbon. XRD analysis of the spent catalyst samples showed that the UZM-35 structure was stable under catalytic conditions. UZM-35 can be regenerated by calcination in air at 550° C. for 3 h. XRD analysis showed that UZM-35 was still intact.

For butene cracking tests, 5 g of meshed catalyst was loaded into the reactor and a 60/40 isobutane/isobutene mixture contacted with the catalyst bed at 7 psig, 27 to 40 WHSV, 520 to 580° C. Results of the butene cracking tests are shown in Table 3.

TABLE 3

| Catalyst | Temperature (° C.) | WHSV | Conversion (wt %) | Light Paraffin Selectivity | Ethylene Selectivity | Propylene Selectivity | Heavies Selectivity |
|---|---|---|---|---|---|---|---|
| Example 6 MFI | 580 | 13.5 | 55 | 10 | 18 | 65 | 17 |

TABLE 3-continued

| Catalyst | Temperature (° C.) | WHSV | Conversion (wt %) | Light Paraffin Selectivity | Ethylene Selectivity | Propylene Selectivity | Heavies Selectivity |
|---|---|---|---|---|---|---|---|
| Example 2 UZM-35 | 520 | 40 | 52 | 10 | 12 | 63.5 | 14.5 |
| Example 2 UZM-35 | 520 | 27 | 60 | 15 | 14 | 49 | 22 |
| Example 2 UZM-35 | 550 | 27 | 70 | 22 | 15 | 36.5 | 26.5 |
| Example 2 UZM-35 | 580 | 27 | 76 | 32 | 12 | 20 | 36 |

Following butene cracking tests, the UZM-35 catalysts were unloaded from the reactor and found to have changed from a white color to black, indicating the presence of C. XRD analysis was performed on these spent samples which showed that the UZM-35 structure was stable under catalytic conditions. UZM-35 can be regenerated by calcination in air at 550° C. for 3 h. XRD analysis shows that UZM-35 is still intact.

Example 7

An aluminosilicate reaction solution was prepared by first mixing 86.33 g of aluminum hydroxide (26.97 mass-% Al) and 1437.67 g of dimethyldipropylammonium hydroxide (40.66 mass-% solution), while stirring vigorously. After thorough mixing, 1366.88 g Ludox™ AS-40 ($SiO_2$, mass-40%) was added. The reaction mixture was homogenized for 20 minutes with a high-speed mechanical stirrer, the aluminosilicate colloidal solution was continuously stirred and an aqueous solution containing 83.04 g of KOH and 17.38 g of NaOH dissolved in 808.7 g $H_2O$ was added, drop wise, to the aluminosilicate solution. After the addition was completed, the resulting reaction mixture was homogenized for ½ hour, transferred to (3) 2000 ml Parr stainless steel autoclave which were heated to 175° C. and maintained at that temperature for 9 days. The solid products were recovered by filtration, washed with de-ionized water, and dried at 100° C.

The product resulting from this reaction was identified by x-ray diffraction (Rietveld refinement method described in J. Appl. Cryst. (1969) 2, 65-71) to be a UZM-35 composition of 72.1 wt-% MSE type zeolite with a lattice parameter of 18.372 angstroms for a and 20.285 angstroms for c; 24.1 wt-% MFI zeolite with a lattice parameter of 20.101 angstroms for a, 19.862 angstroms for b and 13.402 for c, and 3.7 wt-% ERI zeolite with a lattice parameter of 13.222 angstroms for a and 14.900 angstroms for c. Chemical analysis gave a product composition of mole ratio Si/Al 8.9. BET Surface area was determined to be 408 m2/g and micropore volume was 0.197 cc/g. Representative diffraction lines observed for the product are shown in Table 4.

TABLE 4

| 2θ | d(Å) | I/Io % |
|---|---|---|
| 6.5 | 13.58 | m |
| 6.8 | 12.99 | s |
| 7.79 | 11.32 | m |
| 8.07 | 10.93 | m |
| 8.719 | 10.13 | m |
| 9.63 | 9.17 | s |
| 10.75 | 8.21 | w |
| 13.63 | 6.49 | w |
| 14.74 | 6.00 | w |

TABLE 4-continued

| 2θ | d(Å) | I/Io % |
|---|---|---|
| 15.56 | 5.69 | w |
| 15.86 | 5.58 | w |
| 19.46 | 4.55 | m |
| 19.899 | 4.45 | m |
| 20.518 | 4.32 | m |
| 20.94 | 4.23 | w |
| 21.618 | 4.1 | vs |
| 21.799 | 4.07 | s |
| 22.399 | 3.96 | m |
| 22.93 | 3.87 | s |
| 23.299 | 3.81 | m |
| 23.78 | 3.73 | m |
| 24.82 | 3.58 | w |
| 25.76 | 3.45 | w |
| 26.09 | 3.41 | m |
| 26.74 | 3.33 | m |
| 27.42 | 3.24 | m |
| 28.04 | 3.17 | w |
| 29.10 | 3.06 | w |
| 29.54 | 3.02 | w |
| 29.75 | 2.99 | w |
| 30.13 | 2.96 | m |
| 30.73 | 2.9 | m |
| 31.47 | 2.83 | w |
| 33.19 | 2.69 | w |
| 34.46 | 2.6 | w |
| 35.18 | 2.54 | w |
| 35.59 | 2.51 | w |
| 36.04 | 2.49 | w |
| 41.65 | 2.16 | w |
| 44.57 | 2.03 | w |
| 47.48 | 1.91 | w |
| 49.53 | 1.83 | w |

This sample was calcined at 600° C. for 5 hrs under nitrogen and then air. The product resulting from the calcination was identified by x-ray diffraction (Rietveld refinement method described in J. Appl. Cryst. (1969) 2, 65-71) to be a mixture of 64.4 wt % MSE zeolite with a lattice parameter of 18.371 angstroms for a and 20.235 angstroms for c; 30.7 wt % MFI zeolite with a lattice parameter of 20.048 angstroms for a, 19.880 angstroms for b and 13.403 angstroms for c, and 4.8 wt % ERI zeolite with a lattice parameter of 13.071 angstroms for a and 15.238 angstroms for c. A 160 g portion of the calcined UZM-35 sample (Si/Al mole ratio=8.9) was NH4 exchanged. A solution was prepared by dissolving 160 g of $NH_4NO_3$ in 1800 g de-ionized water. The solution was heated to 75° C. before adding the calcined UZM-35. The slurry was stirred for 1 hr at 75° C. The product was isolated by filtration, washed with de-ionized water. This NH4 exchange procedure was repeated 3 times then it was dried at 100° C. for 12 hrs.

Elemental analyses of this sample shows a Si/Al mole ratio to Si/Al=9.07, Na/Al=0.01, K/Al=0.11.

Representative diffraction lines observed for the product are shown in Table 5.

TABLE 5

| 2θ | d(Å) | I/Io % |
|---|---|---|
| 6.67 | 13.22 | m |
| 6.97 | 12.65 | m-s |
| 7.94 | 11.12 | m |
| 8.14 | 10.85 | m |
| 8.93 | 9.88 | m |
| 9.79 | 9.01 | m-s |
| 10.92 | 8.09 | m |
| 13.78 | 6.42 | w |
| 14.1 | 6.27 | w |
| 14.97 | 5.91 | w |
| 15.7 | 5.63 | w |
| 16.05 | 5.51 | w |
| 17.57 | 5.04 | w |
| 19.64 | 4.51 | m |
| 20.05 | 4.42 | m |
| 20.65 | 4.29 | m |
| 21.13 | 4.19 | w |
| 21.77 | 4.07 | vs |
| 21.98 | 4.04 | s-vs |
| 22.62 | 3.92 | s |
| 23.14 | 3.84 | vs |
| 23.46 | 3.78 | m |
| 23.94 | 3.71 | m |
| 24.58 | 3.61 | w |
| 24.83 | 3.58 | w |
| 25.2 | 3.53 | m |
| 25.92 | 3.43 | w |
| 26.24 | 3.39 | m |
| 26.52 | 3.35 | m |
| 26.96 | 3.3 | m |
| 27.6 | 3.22 | m-s |
| 28.25 | 3.15 | m |
| 28.79 | 3.09 | m |
| 29.3 | 3.04 | m |
| 29.68 | 3 | w |
| 29.96 | 2.98 | m |
| 30.35 | 2.94 | m |
| 30.89 | 2.89 | m |
| 31.46 | 2.84 | m |
| 31.81 | 2.81 | m |
| 33.4 | 2.68 | m |
| 36.22 | 2.47 | w |
| 41.83 | 2.15 | w |
| 44.86 | 2.01 | w |
| 47.64 | 1.9 | w |
| 49.69 | 1.83 | w |

Example 8

An aluminosilicate reaction solution was prepared by first mixing 29.01 g of aluminum hydroxide (26.97 wt-% Al) and 483.08 g of dimethyldipropylammonium hydroxide (40.66 wt.-% solution), while stirring vigorously. After thorough mixing, 461.58 g Ludox™ AS-40 ($SiO_2$, 40%) was added. The reaction mixture was homogenized for 20 minutes with a high-speed mechanical stirrer, the aluminosilicate colloidal solution was continuously stirred and an aqueous solution containing 27.90 g of KOH and 3.46 g of NaOH dissolved in 269.98 g $H_2O$ was added, drop wise, to the aluminosilicate solution. After the addition was completed, the resulting reaction mixture was homogenized for ½ hour, transferred to a 2000 ml Parr stainless steel autoclave, which was heated to 175° C. and maintained at that temperature for 10 days. The solid products were recovered by filtration, washed with de-ionized water, and dried at 100° C.

The product resulting from this reaction was identified by x-ray diffraction (Rietveld refinement method described in J. Appl. Cryst. (1969) 2, 65-71) to be a UZM-35 composition of 66.3 wt % MSE type zeolite with a lattice parameter of 18.369 angstroms for a and 20.284 angstroms for c; 25.5 wt % MFI with a lattice parameter of 20.136 angstroms for a, 19.976 angstroms for b and 13.443 angstroms for c, and 8.2 wt % ERI with a lattice parameter of 13.152 angstroms for a and 15.107 angstroms for c. Chemical analysis gave a product composition (mole ratio) of Si/Al=7.65, N/Al=0.38, K/Al=0.68, Na/Al=0.03. BET surface area was determined to be 404 m2/g and a micropore volume was 0.188 cc/g. Representative diffraction lines observed for the product are shown in Table 6.

TABLE 6

| 2θ | d(Å) | I/Io % |
|---|---|---|
| 6.48 | 13.32 | 31.9 |
| 6.78 | 13.02 | 58.5 |
| 8.05 | 10.96 | 25.7 |
| 8.71 | 10.13 | 33.6 |
| 9.61 | 9.18 | 53.6 |
| 10.75 | 8.21 | 11.2 |
| 13.61 | 6.49 | 12.9 |
| 14.74 | 6 | 7.3 |
| 15.86 | 5.58 | 7.2 |
| 19.48 | 4.55 | 41.5 |
| 19.9 | 4.45 | 21.1 |
| 20.5 | 4.32 | 13.4 |
| 20.96 | 4.23 | 25.6 |
| 21.61 | 4.1 | 100 |
| 21.81 | 4.07 | 63.8 |
| 22.42 | 3.96 | 45.7 |
| 22.94 | 3.87 | 85.5 |
| 23.3 | 3.81 | 38.5 |
| 23.5 | 3.78 | 31.3 |
| 23.86 | 3.72 | 17.8 |
| 24.41 | 3.64 | 6.8 |
| 25.78 | 3.45 | 20.2 |
| 26.09 | 3.41 | 19.8 |
| 26.81 | 3.32 | 39.8 |
| 27.14 | 3.28 | 20.9 |
| 27.44 | 3.24 | 42.9 |
| 27.69 | 3.21 | 33 |
| 28.06 | 3.17 | 14.7 |
| 29.15 | 3.06 | 16.2 |
| 29.55 | 3.01 | 13.5 |
| 29.86 | 2.98 | 20.8 |
| 30.14 | 2.96 | 18.7 |
| 30.75 | 2.9 | 24.1 |
| 31.26 | 2.85 | 8.9 |
| 33.21 | 2.69 | 11.1 |
| 34.34 | 2.6 | 8.8 |
| 34.76 | 2.57 | 10.5 |
| 35.2 | 2.54 | 6.8 |
| 35.57 | 2.52 | 8.6 |
| 36.02 | 2.49 | 8 |
| 41.71 | 2.16 | 9.8 |
| 44.61 | 2.02 | 8.2 |
| 47.48 | 1.91 | 8 |
| 49.56 | 1.83 | 10.1 |

This sample was calcined at 600° C. for 5 hrs under nitrogen and then air. The product resulting from the calcination was identified by x-ray diffraction (Rietveld refinement method described in J. Appl. Cryst. (1969) 2, 65-71) to be a UZM-35 composition of 61.9 wt-% MSE zeolite with a lattice parameter of 18.401 angstroms for a and 20.280 angstroms for c; 30.8 wt-% MFI zeolite with a lattice parameter of 20.114 angstroms for a, 19.919 angstroms for b and 13.432 angstroms for c, and 7.3-wt % ERI zeolite with a lattice parameter of 13.189 angstroms for a and 15.174 angstroms for c. A 100 g portion of the calcined UZM-35 sample (Si/Al mole ratio=7.65) was NH4 exchanged. A solution was prepared by dissolving 160 g of $NH_4NO_3$ in 1800 g de-ionized water. The solution was heated to 75° C. before adding the calcined UZM-35. The slurry was stirred for 1 hr at 75° C. The product was isolated by filtration, washed with de-ionized water. This NH4 exchange procedure was repeated 3 times then it was dried at 100° C. for 12 hrs.

Elemental analyses of this sample shows a Si/Al mole ratio to Si/Al=9.20, Na/Al=0.01, K/Al=0.10.

Representative diffraction lines observed for the product are shown in Table 7.

TABLE 7

| 2θ | d(Å) | I/Io % |
|---|---|---|
| 6.5 | 13.58 | m |
| 6.81 | 12.95 | m |
| 7.98 | 11.07 | m |
| 8.76 | 10.08 | m |
| 9.63 | 9.16 | m |
| 10.77 | 8.2 | m |
| 13.63 | 6.48 | m |
| 14.8 | 5.98 | w |
| 15.84 | 5.58 | w |
| 19.51 | 4.54 | m |
| 19.91 | 4.45 | m |
| 20.49 | 4.32 | m |
| 21.01 | 4.22 | m |
| 21.62 | 4.1 | vs |
| 22.49 | 3.94 | s |
| 23.02 | 3.86 | vs |
| 23.3 | 3.81 | m-s |
| 23.64 | 3.76 | m |
| 23.91 | 3.71 | m |
| 24.41 | 3.64 | m |
| 24.62 | 3.61 | w |
| 25.11 | 3.54 | w |
| 25.81 | 3.44 | m |
| 26.09 | 3.41 | m |
| 26.41 | 3.37 | m |
| 26.86 | 3.31 | m-s |
| 27.45 | 3.24 | m-s |
| 27.65 | 3.22 | m |
| 28.13 | 3.16 | m |
| 28.82 | 3.09 | w |
| 29.14 | 3.06 | m |
| 29.57 | 3.01 | w |
| 29.84 | 2.99 | m |
| 30.21 | 2.95 | m |
| 30.76 | 2.9 | m |
| 31.31 | 2.85 | w |
| 33.27 | 2.69 | w |
| 36.12 | 2.48 | w |
| 41.68 | 2.16 | w |
| 44.74 | 2.02 | w |
| 47.56 | 1.91 | w |
| 49.57 | 1.83 | w |

The invention claimed is:

1. A process for catalytic cracking comprising contacting a hydrocarbon feedstock with a catalyst at catalytic cracking conditions and producing a cracked product wherein the catalyst comprises a UZM-35 microporous crystalline zeolitic composition comprising at least a MSE type zeolite, a MFI type zeolite, and an ERI type zeolite, wherein the UZM-35 composition has a three-dimensional framework of at least $AlO_2$ and $SiO_2$ tetrahedral units and an empirical composition in the as synthesized and anhydrous basis expressed by an empirical formula of:

$$M_m{}^+R_rAl_{1-x}E_xSi_yO_z$$

where M represents a combination of potassium and sodium exchangeable cations, "m" is the mole ratio of M to (Al+E) and varies from about 0.05 to about 3, R is a singly charged dimethyldipropylammonium cation, "r" is the mole ratio of R to (Al+E) and has a value of about 0.25 to about 2.0, E is an element selected from the group consisting of gallium, iron, boron and mixtures thereof, "x" is the mole fraction of E and has a value from 0 to about 1.0, "y" is the mole ratio of Si to (Al+E) and varies from greater than 2 to about 12 and "z" is the mole ratio of O to (Al+E) and has a value determined by the equation:

$$z=(m+r+3+4\cdot y)/2$$

and is characterized in that it has the x-ray diffraction pattern having at least the d-spacings and intensities set forth in Table A':

TABLE A'

| 2θ | d(Å) | I/Io % |
|---|---|---|
| 6.48-6.51 | 13.32-13.58 | m |
| 6.78-6.83 | 12.91-13.02 | m-s |
| 7.79-7.96 | 11.09-11.32 | m |
| 8.05-8.07 | 10.93-10.96 | m |
| 8.71-8.75 | 10.08-10.13 | m |
| 9.61-9.65 | 9.15-9.18 | m-s |
| 10.75-10.79 | 8.18-8.21 | w |
| 13.61-13.65 | 6.47-6.49 | w |
| 14.74-14.79 | 5.98-6 | w |
| 15.56-15.59 | 5.67-5.69 | w |
| 15.86-15.86 | 5.58-5.58 | w |
| 19.46-19.5 | 4.54-4.55 | m |
| 19.89-19.92 | 4.45-4.45 | m |
| 20.48-20.51 | 4.32-4.33 | m |
| 20.94-20.96 | 4.23-4.23 | m |
| 21.61-21.64 | 4.1-4.1 | vs |
| 21.79-21.81 | 4.07-4.07 | s |
| 22.39-22.45 | 3.95-3.96 | m |
| 22.93-22.98 | 3.86-3.87 | s-vs |
| 23.29-23.31 | 3.81-3.81 | m |
| 23.5-23.5 | 3.78-3.78 | m |
| 23.78-23.86 | 3.72-3.73 | m |
| 24.39-24.41 | 3.64-3.64 | w |
| 24.82-24.82 | 3.58-3.58 | w |
| 25.76-25.79 | 3.45-3.45 | w-m |
| 26.09-26.12 | 3.4-3.41 | m |
| 26.74-26.81 | 3.32-3.33 | m |
| 27.14-27.14 | 3.28-3.28 | m |
| 27.42-27.46 | 3.24-3.249 | m |
| 27.69-27.69 | 3.21-3.21 | m |
| 28.02-28.06 | 3.17-3.18 | m |
| 29.1-29.15 | 3.06-3.06 | m |
| 29.54-29.61 | 3.01-3.02 | w |
| 29.75-29.86 | 2.98-2.99 | w |
| 30.12-30.14 | 2.96-2.96 | m |
| 30.73-30.79 | 2.9-2.9 | m |
| 31.26-31.27 | 2.85-2.85 | w |
| 31.47-31.47 | 2.83-2.83 | w |
| 33.19-33.25 | 2.69-2.69 | w |
| 34.34-34.48 | 2.59-2.6 | w |
| 34.76-34.76 | 2.57-2.57 | w |
| 35.18-35.2 | 2.54-2.54 | w |
| 35.57-35.59 | 2.51-2.52 | w |
| 36.02-36.04 | 2.48-2.49 | w |
| 41.65-41.71 | 2.16-2.16 | w |
| 44.57-44.61 | 2.02-2.03 | w |
| 47.48-47.58 | 1.9-1.91 | w |
| 49.53-49.59 | 1.83-1.83 | w | and is thermally stable up to a temperature of at least 400° C.

2. The process of claim 1 wherein the feedstock has an initial boiling point of greater than 200° C.

3. The process of claim 2 where the feedstock is selected from the group consisting of gas oils, heavy naphtha, cycle oils, deasphalted crude oil residua, Fischer-Tropsch wax, slack wax, hydrotreated gas oils, hydrotreated heavy naphtha, hydrotreated cycle oils, hydrotreated deasphalted crude oil residua, hydrotreated Fischer-Tropsch wax, hydrotreated slack wax, and combinations thereof.

4. The process of claim 2 where said catalytic cracking conditions include a temperature of from 400° C. to 800° C., a pressure of from about 0 to 688 kPag (about 0 to 100 psig) and a contact time of from about 0.1 seconds to about 1 hour.

5. The process of claim 1 wherein the MSE type zeolite is present in an amount from about 55 wt % to about 90 wt. % of the UZM-35 composition.

6. The process of claim 1 wherein the MFI type zeolite is present in an amount from about 10 wt-% to about 35 wt-% of the UZM-35 composition.

7. The process of claim 1 wherein the ERI type zeolite is present in an amount from about 3 wt-% to about 10 wt-% of the UZM-35 composition.

8. The process of claim 4 wherein the catalyst further comprises one or more zeolites of the FAU structure type, one or more zeolites of an additional MFI structure types, or combinations thereof.

9. The process of claim 8 where the weight ratio of UZM-35 composition to the one or more zeolites of the FAU or additional MFI structure types is from about 0.01 to about 50.

10. The process of claim 8 where the weight ratio of UZM-35 to the one or more zeolites of the FAU or additional MFI structure types is from about 0.01 to about 1.11.

11. The process of claim 1 wherein "x" of the UZM-35 composition is zero.

12. The process of claim 1 where R is a combination of dimethyldipropyl ammonium hydroxide and at least one singly charged organoammonium cation selected from the group consisting of TEA, TPA, ETMA, DEDMA, trimethylpropylammonium, dimethyldiisopropyl ammonium, trimethylbutylammonium, dimethyldiethanolammonium, and methyltripropylammonium.

13. The process of claim 1 wherein the feedstock comprises a naphtha having a boiling range of about 25° C. to about 225° C.

14. The process of claim 8 where said catalytic cracking conditions include a temperature of from about 400° C. to about 700° C., a pressure of from about 0 to about 688 kPag (about 0 to 100 psig) and a contact time of from about 0.1 seconds to about 1 hour.

15. A process for catalytic cracking comprising contacting an olefin containing hydrocarbon feedstock with a catalyst at catalytic cracking conditions and producing a cracked product wherein the catalyst comprises a UZM-35 microporous crystalline zeolitic composition comprising at least a MSE type zeolite, a MFI type zeolite, and an ERI type zeolite, wherein the UZM-35 composition has a three-dimensional framework of at least $AlO_2$ and $SiO_2$ tetrahedral units and an empirical composition in the as synthesized and anhydrous basis expressed by an empirical formula of:

$$M_m^{n+}R_rAl_{1-x}E_xSi_yO_z$$

where M represents a combination of potassium and sodium exchangeable cations, "m" is the mole ratio of M to (Al+E) and varies from about 0.05 to about 3, R is a singly charged dimethyldipropylammonium cation, "r" is the mole ratio of R to (Al+E) and has a value of about 0.25 to about 2.0, E is an element selected from the group consisting of gallium, iron, boron and mixtures thereof, "x" is the mole fraction of E and has a value from 0 to about 1.0, "y" is the mole ratio of Si to (Al+E) and varies from greater than 2 to about 12 and "z" is the mole ratio of O to (Al+E) and has a value determined by the equation:

$$z=(m+r+3+4 \cdot y)/2$$

and is characterized in that it has the x-ray diffraction pattern having at least the d-spacing's and intensities set forth in Table A':

TABLE A'

| 2θ | d(Å) | I/Io % |
|---|---|---|
| 6.48-6.51 | 13.32-13.58 | m |
| 6.78-6.83 | 12.91-13.02 | m-s |
| 7.79-7.96 | 11.09-11.32 | m |
| 8.05-8.07 | 10.93-10.96 | m |
| 8.71-8.75 | 10.08-10.13 | m |
| 9.61-9.65 | 9.15-9.18 | m-s |
| 10.75-10.79 | 8.18-8.21 | w |
| 13.61-13.65 | 6.47-6.49 | w |
| 14.74-14.79 | 5.98-6 | w |
| 15.56-15.59 | 5.67-5.69 | w |
| 15.86-15.86 | 5.58-5.58 | w |
| 19.46-19.5 | 4.54-4.55 | m |
| 19.89-19.92 | 4.45-4.45 | m |
| 20.48-20.51 | 4.32-4.33 | m |
| 20.94-20.96 | 4.23-4.23 | m |
| 21.61-21.64 | 4.1-4.1 | vs |
| 21.79-21.81 | 4.07-4.07 | s |
| 22.39-22.45 | 3.95-3.96 | m |
| 22.93-22.98 | 3.86-3.87 | s-vs |
| 23.29-23.31 | 3.81-3.81 | m |
| 23.5-23.5 | 3.78-3.78 | m |
| 23.78-23.86 | 3.72-3.73 | m |
| 24.39-24.41 | 3.64-3.64 | w |
| 24.82-24.82 | 3.58-3.58 | w |
| 25.76-25.79 | 3.45-3.45 | w-m |
| 26.09-26.12 | 3.4-3.41 | m |
| 26.74-26.81 | 3.32-3.33 | m |
| 27.14-27.14 | 3.28-3.28 | m |
| 27.42-27.46 | 3.24-3.249 | m |
| 27.69-27.69 | 3.21-3.21 | m |
| 28.02-28.06 | 3.17-3.18 | m |
| 29.1-29.15 | 3.06-3.06 | m |
| 29.54-29.61 | 3.01-3.02 | w |
| 29.75-29.86 | 2.98-2.99 | w |
| 30.12-30.14 | 2.96-2.96 | m |
| 30.73-30.79 | 2.9-2.9 | m |
| 31.26-31.27 | 2.85-2.85 | w |
| 31.47-31.47 | 2.83-2.83 | w |
| 33.19-33.25 | 2.69-2.69 | w |
| 34.34-34.48 | 2.59-2.6 | w |
| 34.76-34.76 | 2.57-2.57 | w |
| 35.18-35.2 | 2.54-2.54 | w |
| 35.57-35.59 | 2.51-2.52 | w |
| 36.02-36.04 | 2.48-2.49 | w |
| 41.65-41.71 | 2.16-2.16 | w |
| 44.57-44.61 | 2.02-2.03 | w |
| 47.48-47.58 | 1.9-1.91 | w |
| 49.53-49.59 | 1.83-1.83 | w | and is thermally stable up to a temperature of at least 400° C.

16. The process of claim 15 wherein the olefin containing feedstock comprises from about C4 to about C10 olefins.

17. The process of claim 16 where said catalytic cracking conditions include a temperature of from 400° C. to 650° C., a pressure of from about 0 to 344 kPag (about 0 to 50 psig) and a contact time of from about 0.1 seconds to about 1 hour.

18. The process of claim 17 wherein the cracked product comprises ethylene, propylene and butylene.

19. The process of claim 15 wherein "x" of the UZM-35 composition is zero.

20. The process of claim 15 where R is a combination of dimethyldipropyl ammonium hydroxide and at least one singly charged organoammonium cation selected from the group consisting of TEA, TPA, ETMA, DEDMA, trimethylpropylammonium, trimethylbutylammonium, dimethyldiethanolammonium, dimethyldiisopropyl ammonium, and methyltripropylammonium.

* * * * *